United States Patent [19]

Miyata et al.

[11] Patent Number: 5,962,299
[45] Date of Patent: Oct. 5, 1999

[54] METHOD OF STABILIZING PROTEIN C OR ACTIVATED PROTEIN C AND THE STABILIZED COMPOSITION OBTAINED BY SAID METHOD

[75] Inventors: Kazumasa Miyata; Yoshinori Akimoto; Yoichi Ogata, all of Kumamoto; Tomohiro Nakagaki, Kikuchi-gun, all of Japan

[73] Assignees: Juridical Foundation The Chemo-Sero-Therapeutic Research Institute, Kumamoto; Teijin Limited, Osaka, both of Japan

[21] Appl. No.: 08/633,834

[22] PCT Filed: Oct. 27, 1994

[86] PCT No.: PCT/JP94/01804

§ 371 Date: Apr. 23, 1996

§ 102(e) Date: Apr. 23, 1996

[87] PCT Pub. No.: WO95/11698

PCT Pub. Date: May 4, 1995

[30] Foreign Application Priority Data

Oct. 29, 1993 [JP] Japan ..................................... 5-292500

[51] Int. Cl.$^6$ ............................... C12N 9/48; C12N 9/96
[52] U.S. Cl. ........................................... 435/212; 435/188
[58] Field of Search ...................................... 435/212, 188

[56] References Cited

U.S. PATENT DOCUMENTS 5,549,893  8/1996  Eibl et al. .

FOREIGN PATENT DOCUMENTS

| 514367 | 11/1992 | European Pat. Off. . |
| 726311 | 8/1996 | European Pat. Off. . |
| 5-132427 | 5/1993 | Japan . |
| 5-17066 | 7/1993 | Japan . |
| 5-170665 | 7/1993 | Japan . |
| 7165605 | 6/1995 | Japan . |

OTHER PUBLICATIONS

McIntosh, R. and Foster, P., *The Effect of Solution Formulation on the Stability and Surface Interactions of Factor VIII During Plasma Fractionation, Transfus, Sci.*, 11:55–66; 1990.

Primary Examiner—Leon B. Lankford, Jr.
Attorney, Agent, or Firm—Browdy and Neimark

[57] ABSTRACT

A method for stabilizing protein C or activated protein C and a preparation obtained by said method are provided, said method and preparation being applicable during procedures such as isolation and purification, lyophilization, heating, etc. or when stored.

To a salt buffer containing protein C or activated protein C and sodium ion are added at least one amino acids, and further either one or a combination of albumin and a non-ionic surfactant.

19 Claims, No Drawings

METHOD OF STABILIZING PROTEIN C OR ACTIVATED PROTEIN C AND THE STABILIZED COMPOSITION OBTAINED BY SAID METHOD

TECHNICAL FIELD OF THE INVENTION

The present invention relates to a method for stabilizing protein C or activated protein C which is derived from plasma or is prepared by using the genetic recombination technique. More particularly, the present invention relates to a method for stabilizing protein C or activated protein C when it is stored or subjected to procedures such as isolation and purification, lyophilization, treatment by heating, etc. and to a preparation stabilized by said method.

TECHNICAL BACKGROUND

Protein C (hereinafter also referred to as "PC") is a kind of a vitamin K dependent protein, i.e. a protein containing γ-carboxyglutamic acid, and is activated to activated protein C (hereinafter also referred to as "APC") by thrombin in the presence of thrombomodulin present on the surface of the vascular endothelial cell. Activated protein C is a kind of a serine protease and exhibits a strong anti-coagulant activity by inactivating cofactors of the blood coagulation system such as Factor Va (FVa) and Factor VIIIa (FVIIIa). It is also known that activated protein C releases a plasminogen activator from the vascular wall to accelerate the fibrinolytic system. Furthermore, it is known that a defect in protein C causes a severe thrombosis. Thus, it has been established that activated protein C is the most important factor which regulates the blood coagulation and fibrinolytic system. Therefore, protein C or activated protein C is expected to be exploited as a novel anti-coagulating agent or profibrinolytic agent.

It has hitherto been known that the amount of protein C present in a plasma or expressed in a tissue culture system is extremely low. Accordingly, in order to use protein C or activated protein C as an anti-coagulant agent or a profibrinolytic agent widely and safely, isolation and purification of protein C or activated protein C is important. In addition, storage as a solution or in frozen form for long periods of time, lyophilization or procedures for inactivation of contaminating viruses such as heating are indispensable to the process when protein C or activated protein C is industrially prepared on a large scale. However, storage, freezing or freeze-drying, or heat treatment of a highly pure protein C or activated protein C extremely lowers the activity thereof. There has also been no report on the stability of highly purified protein C or activated protein C. Under such circumstances, it is impossible to provide a highly pure protein C or activated protein C efficiently and stably on an industrial scale.

Under such circumstances, the present inventors have earnestly studied the stability of protein C or activated protein C, and as a result, have found that the activity of protein C or activated protein C can be maintained even after storage for a significant period of time or after procedures such as isolation and purification, lyophilization, heating, etc. by adding, to protein C or activated protein C, a salt buffer such as phosphate or citrate buffer containing sodium ion supplemented with at least one amino acid, and further adding either one or a combination of albumin and a non-ionic surfactant, and thereby, the present invention has been completed.

DISCLOSURE OF THE INVENTION

The present invention relates to a method for stabilizing protein C or activated protein C which comprises adding, to a salt buffer containing protein C or activated protein C and sodium ion, at least one amino acid, and further either one or a combination of albumin and a non-ionic surfactant. More particularly, the present invention relates to a method for stabilizing protein C or activated protein C which comprises dissolving protein C or activated protein C in a salt buffer such as phosphate or citrate buffer containing sodium ion, and adding to said buffer at least one of amino acids which constitute a protein, e.g. glycine, alanine, lysine, arginine, aspartic acid, glutamic acid, etc. and a polypeptide having a protein-stabilizing activity such as albumin, globulin, etc. and, in a preferable embodiment, optional non-ionic surfactant, typically Tween 80 is added. The invention also relates to preparations stabilized by said method.

BEST MODE FOR CARRYING OUT THE INVENTION

Protein C or activated protein C used herein encompasses variants or derivatives thereof which substantially has APC activity and may be prepared by the known methods, for example, by preparing protein C by isolation from human plasma or production utilizing the genetic recombination technique and then activating protein C; by directly isolating APC from human blood; or by producing APC by the use of the genetic recombination technique, etc. Activation of protein C into APC can be carried out by any known method, for example, by activation with thrombin isolated from human or bovine blood, or by activation with an equivalent protease, etc.

Production of APC derived from blood can be conducted, for example, by activating protein C, which is purified from human plasma by affinity chromatography using an anti-protein C antibody, with human thrombin, and purifying the resulting activated protein C by a cation chromatography (Blood, 63, p.115–121 (1984)); or by activating protein C which is purified from human plasma by barium citrate adsorption and elution, fractionation with ammonium sulfate, DEAE-Sephadex column chromatography, dextran sulfate agarose chromatography and polyacrylamide gel electrophoresis, etc. to produce APC in accordance with the method described by Kisiel (J. Clin. Invest., 64, p.761–769 (1979)); or by activating a commercially available blood-coagulating preparation containing protein C to produce APC in accordance with the method described by Taylor et al. (J. Clin. Invest., 79, p.918–925 (1987)), and the like.

Production of APC utilizing the genetic recombination technique can be conducted, for example, in accordance with the methods described in Japanese Patent First Publication (Kokai) No. 61-205487, Japanese Patent First Publication (Kokai) No. 1-2338 or Japanese Patent First Publication (Kokai) No. 1-85084, etc. A process for preparing the starting material protein C or activated protein C as used herein is not limited to the above-mentioned procedures.

The thus prepared starting material protein C or activated protein C is isolated and purified by a combination of usual biochemical procedures for isolation and purification, including, for example, a salting-out with ammonium sulfate, an ion-exchange chromatography with an ion exchange resin, gel filtration, electrophoresis, etc.

When the degree of purification is increased by such procedures, protein C or activated protein C is liable to become unstable. Even a product having not so much high purity also shows a decrease in the activity due to the procedures such as storage, freezing, lyophilization, heating, etc. The present invention is primarily aimed at the stabilization of such protein C or activated protein C which became unstable with the increase of purification degree. Protein C or activated protein C to be stabilized in accordance with the present invention may be either in the form of solution or powder.

In the stabilization method for protein C or activated protein C of the present invention, a salt containing as a stabilizing agent sodium ion at a concentration of preferably 50 mM to 200 mM, at least one amino acid and a polypeptide having a stabilizing effect are added to a buffer containing 100 to 2500 U/ml of protein C or activated protein C. The salt and amino acid may be used each alone or in a combination of two or more thereof. Preferable buffer includes, for example, sodium citrate, sodium phosphate, and sodium sulfate, etc. The amino acid is added at a final concentration of 0.005 M to 0.1 M, more preferably 0.01 M to 0.05 M. A polypeptide having a stabilizing effect such as albumin or globulin is added at an appropriate concentration which may be determined based on a common sense or from the economical point of view, preferably at a concentration of 0.5% (W/V) to 10% (W/V). The unit "% (W/V)" as used herein denotes an amount of a solute dissolved in one liter of a solution, for example, when 10 g of a solute is dissolved in one liter of a solution, a concentration is 1% (W/V). In a preferable embodiment of the present invention, a non-ionic surfactant such as Tween 80 may optionally be added at a concentration of 0.0005% (W/V) to 0.1% (W/V) to accelerate the stabilization effect.

A typical embodiment of the present invention is an aqueous buffer solution containing protein C or activated protein C, which comprises 100 to 2500 U/ml of protein C and/or activated protein C, 50 to 200 mM of sodium ion, 5 to 100 mM of an amino acid, and further either one or a combination of 0.5 to 10% (W/V) of albumin and 0.0005 to 0.1% (W/V) of a non-ionic surfactant.

When a stabilizing agent is added to protein C or activated protein C in the form of powder, it is used in such an amount that the concentration of the stabilizing agent becomes in the above-mentioned range when said powder is dissolved.

Thus, in another typical embodiment of the present invention, a composition containing protein C or activated protein C comprises $1 \times 10^5$ to $2.5 \times 10^6$ U of protein C and/or activated protein C, 50 to 200 mg of sodium ion, 5 to 100 millimoles of an amino acid, and further either one or a combination of 5 to 100 g of albumin and 0.005 to 1 g of a non-ionic surfactant.

The manner of addition of these ingredients may not be specified but includes various methodes, for example, by adding directly powdery materials of the present invention to a buffer solution containing protein C or activated protein C; or by previously dissolving said powdery materials in water or a suitable buffer and adding the solution to the buffer solution containing protein C or activated protein C; or by mixing said powdery materials with a protein C- or activated protein C-containing powder. Addition may be carried out either during the process of isolation and purification of said protein or the process for producing a pharmaceutical preparation.

When a solution containing protein C or activated protein C added with the stabilizing agent of the present invention is stored, or subjected to procedures such as isolation and purification, or process for producing a pharmaceutical preparation in the state of solution, it is preferably done at 0 to 30° C., more preferably at 0 to 10° C. When said solution is stored in a freezed state, it is preferably done at a lower temperature than the freezing point, more preferably at lower than –20° C., or when it is stored in a lyophilized state, it is preferably done at room temperature or lower. By using the solution containing protein C or activated protein C incorporated with the stabilizing agent of the present invention, the activity of protein C or activated protein C can be stably maintained even during storage in the state of a solution, or in a freezed or lyophilized state, or even in the treatment thereof such as isolation and purification or process for producing a pharmaceutical preparation.

The activity of APC was measured in accordance with the following procedures.

One unit of APC activity is defined as an amount of APC which prolongs twice an activated thromboplastin time (APTT; second) of normal human plasma. Accordingly, the activity of APC is measured wherein APTT in seconds is measured for normal human plasma to which a diluted sample is added and the dilution at which the measured APTT value is twice that of control (buffer) is determined and regarded as the activity of APC for samples.

(Procedures)

A sample is diluted with a veronal buffer containing 1% human serum albumin to, for example, 400 times, 500 times, 800 times or 1000 times dilution. To each 100 µl of either control (buffer) or samples of each dilution are added 100 µl of normal human plasma (e.g. Citrol I: Baxter Diagnostics Inc.) 100 µl and APTT reagent (e.g. Actin: Baxter Diagnostics Inc.) 100 µl at 37° C. successively with an interval of 15 seconds, the mixture is stirred, and after 2 minutes, 0.025 M CaCl$_2$ 100 µl is added and the coagulation time is measured.

(Calculation of Activity)

A linear regression formula and a correlation coefficient of $10^3/X$ and Y are obtained from the APTT values (Y) at each dilution (X) of the control and the samples as follows:

$$Y = A(10^3/X) + B$$

A value of $X_1$ obtained from the following formula:

$$X_1 = 10^3\{(Y_1 - B)/A\}$$

wherein $Y_1$ is a value twice that of the APTT (second) of control, is regarded as the activity of APC (U/ml) for samples.

The activity of protein C was measured by using "Staclot Protein C" manufactured by Boehlinger Mannheim.

The present invention is illustrated in more detail by means of the following Examples but should not be construed to be limited thereto.

EXAMPLE 1

Effect of Various Counterions on Stability of APC:

To a solution containing human activated protein C with the activity of 500 U/ml was added 2.5% human serum albumin (hereinafter also abbreviated as "HSA"). The solution was then dialyzed against a solution of Na citrate, Na phosphate and Na sulfate (each 20 mM), containing 0.7% NaCl and 0.067 M glycine. After dialysis, each solution was left to stand at 37° C. for 24 hours and the activity was measured. The results are shown in Table 1. All the counterions tested, Na citrate, Na phosphate and Na sulfate, showed a similar satisfactory stability.

TABLE 1

Effect of various counterions on stability of APC

| Counterion | Rate of remaining activity (%) (37° C., 24 hours) |
| --- | --- |
| Na citrate 20 mM | 97.4 |
| Na phosphate 20 mM | 94.8 |
| Na sulfate 20 mM | 92.2 |

EXAMPLE 2

Effect of Amino Acids on Stability of APC:

To a solution containing activated protein C with the activity of 500 U/ml was added 2.5% HSA. The solution was then dialyzed against a solution of sodium citrate buffer containing 0.7% NaCl and each 0.05 M of either glycine, alanine, lysine, arginine, aspartic acid or glutamic acid. After dialysis, each solution was left to stand at 37° C. for 24 hours and the activity was measured. The results are shown in Table 2. All the above six amino acids showed a high stability without deteriorating the stability of APC.

TABLE 2

Effect of various amino acids on stability of APC

| Amino Acid (0.5%) | Rate of remaining activity (%) (37° C., 24 hours) |
| --- | --- |
| No amino acid | 86.1 |
| Gly | 97.7 |
| Ala | 97.7 |
| Lys | 107 |
| Arg | 102 |
| Asp | 108 |
| Glu | 106 |

EXAMPLE 3

Effect of Addition of HSA:

Solutions containing human activated protein C (1700 U/ml), 20 mM citrate, 0.7% NaCl and 0.067 M glycine with and without addition of 2.5% HSA were prepared. The solutions were then left to stand at 37° C. and 4° C. The activity was measured with the passage of time in accordance with the method described herein and a retention percent of activity was obtained. The results are shown in Table 3.

TABLE 3

Retention percent of activity under respective conditions (%)

At 37° C.:

| | Retention time (hour) | | | | |
| --- | --- | --- | --- | --- | --- |
| | 0 | 1 | 3 | 6 | 8 | 24 |
| HSA (+) | 100 | — | 99.2 | — | 101 | 97.4 |
| HSA (−) | 100 | 88.8 | 92.0 | 86.2 | 90.9 | 79.3 |

TABLE 3-continued

Retention percent of activity under respective conditions (%)

At 4° C.:

| | Retention time (day) | | | | |
| --- | --- | --- | --- | --- | --- |
| | 0 | 1 | 3 | 5 | 7 | 14 |
| HSA (+) | 100 | — | 105 | — | — | 98.1 |
| HSA (−) | 100 | 112 | 99.1 | 104 | 98.9 | 85.2 |

As will be understood from the results shown in Table 3, the system without HSA can not prevent decrease in the activity of APC when it is left standing. From these results, it is concluded that 2.5% HSA extremely stabilizes APC.

EXAMPLE 4

Effect of HSA on Stability of APC:

The data shown in Table 4 indicates that the activity of APC is dependent on the concentration of HSA. To a solution of activated protein C (500 U/ml) was added 0.5 to 10.0% HSA. This solution was put in a storage vessel and left to stand at 37° C. After 24 hours, a sample was taken and the activity was measured. In case of no addition of HSA, the activity was decreased by about 20% whereas in case of addition of HSA at a concentration ranging from 0.5 to 10.0%, almost no decrease in the activity was observed and APC remained stable.

TABLE 4

Effect of HSA on stability of APC activity

| HSA (%) | Rate of remaining activity (%) (37° C., 24 hours) |
| --- | --- |
| 0.0 | 79.0 |
| 0.5 | 96.0 |
| 2.5 | 97.4 |
| 5.0 | 98.0 |
| 10.0 | 102 |

EXAMPLE 5

Effect of Tween 80 on Stability of APC:

To a solution containing human activated protein C (500 U/ml), 20 mM citrate, 0.7% NaCl and 0.067 M glycine was added 0.0005% to 0.1% non-ionic surfactant, Tween 80 (trade name). This solution was put in a storage vessel and left to stand at 37° C. After 24 hours, a sample was taken and the activity was measured. The results are shown in Table 5. In case of no addition of Tween 80, the activity was decreased by about 20% and the stability was deteriorated whereas in case of addition of Tween 80 at a concentration ranging from 0.0005 to 0.1%, no change in the activity was found and the solution maintained high stability.

TABLE 5

| Tween 80 (%) | Rate of remaining activity (%) (37° C., 24 hours) |
| --- | --- |
| No addition | 79 |
| 0.0005 | 101 |
| 0.025 | 104 |
| 0.1 | 103 |

EXAMPLE 6
Effect of NaCl on Quality of Lyophilized Solid Citrate:

An APC lyophilized preparation containing APC 500 U/ml, HSA 2.5%, Gly 0.067 M and Na citrate 20 mM was prepared such that it contains sodium chloride at a concentration ranging from 1 mM to 500 mM. Each lyophilized preparation was stored at 60° C. for a month and the appearance quality of the solids was observed as shown in Table 6.

TABLE 6

Quality of lyophilized preparation containing NaCl at a selected concentration

| Na chloride (mM) | Quality of solids | |
|---|---|---|
| | Pre-storage | After One month storage at 60° C. |
| 1 | White solid, shrink | Extremely shrink |
| 10 | White solid, a bit shrink | Same as pre-storage |
| 50 | White porous lump | Same as pre-storage |
| 100 | White porous lump | Same as pre-storage |
| 500 | Glassy shrunk lump | Same as pre-storage |

As is clear from the results shown in Table 6, a solids APC preparation is difficult to formulate into a pharmaceutical preparation in the case of addition of sodium chloride both at a higher and lower concentration. The presence of sodium chloride at a concentration of 50 mM to 200 mM is considered to contribute to the stabilization of the lyophilized preparation.

EXAMPLE 7
APC Activity in Lyophilized Preparation:

A citrate buffer solution containing the stabilizing agent of the present invention (0.7% NaCl, 0.067 M glycine and 2.5% HSA) was prepared so that it contains the APC activity at 100 to 2500 U/vial and sterilely divided into vials, which were lyophilized and sealed. Each vial was left to stand at 10° C., 15° C. and 60° C. and decrease in the activity was determined. The results are shown in Table 7. The data show that the method for stabilization of APC of the present invention is effective in the state of lyophilization.

TABLE 7

| APC (U/vial) | Time | Rate of remaining activity (%) | | |
|---|---|---|---|---|
| | | 10° C. | 15° C. | 60° C. |
| 100 | 30 months | 100 | 101 | — |
| 500 | 30 months | 97 | 99 | — |
| | 11 days | | | 99 |
| 1000 | 30 months | 99 | 97 | — |
| 2500 | 30 months | 98 | 95 | — |
| | 11 days | | | 105 |

EXAMPLE 8
Effect Repeated Freezing-melting on the Stability of APC:

To a citrate buffer solution containing activated protein C with the activity of 500 U/ml was added the stabilizing agent of the present invention (0.7% NaCl, 0.067 M glycine and 2.5% HSA). The resulting solution was subjected to repetition (5 times, 10 times, 15 times and 20 times) of freezing (−80° C.) and melting and the activity was measured. The results are shown in Table 8. In spite of 20 repetitions of freezing-melting, the activity of APC showed no significant change and remained stable.

TABLE 8

| Repetition | Rate of maintaining activity (%) |
|---|---|
| 5 | 102 |
| 10 | 95.1 |
| 15 | 106 |
| 20 | 99.2 |

What is claimed is:

1. A method for stabilizing protein C or activated protein C which comprises adding a salt buffer, a sodium salt for a final concentration of 50 to 100 mM of sodium ion, at least one amino acid for a final concentration of 0.005M to 0.1M, and a compound selected from the group consisting of albumin for a final concentration of 0.5 to 10% w/v, a non-ionic surfactant for a final concentration of 0.0005 to 0.1% w/v, and a mixture thereof, to protein C or activated protein C to form a protein C or activated protein C-containing composition in which protein C or activated protein C is stable at 37° C. for 24 hours.

2. The method for stabilizing protein C or activated protein C of claim 1, wherein said at least one amino acid is selected from the group consisting of natural occurring α-amino acids.

3. The method for stabilizing protein C or activated protein C of claim 2 wherein said at least one amino acid is selected from glycine, alanine, lysine, arginine, aspartic acid, glutamic acid, and mixtures thereof.

4. An aqueous buffer solution containing protein C and/or activated protein C which contains 100 to 2500 U/ml of protein C and/or activated protein C, 50 to 200 mM of sodium ion, 5 to 100 mM of an amino acid, and further either one or a combination of 0.5 to 10% (w/v) of albumin and 0.0005 to 0.1% (w/v) of a non-ionic surfactant, wherein said protein C and/or activated protein C is stable in said aqueous buffer solution at 37° C. for 24 hours.

5. A composition containing protein C and/or activated protein C which contains $1 \times 10^5$ to $2.5 \times 10^6$ U of protein C and/or activated protein C, 50 to 200 mg of sodium ion, 5 to 100 millimoles of an amino acid, and further either one or a combination of 5 to 100 g of albumin and 0.005 to 1 g of a non-ionic surfactant, wherein said protein C and/or activated protein C is stable in said composition at 37° C. for 24 hours.

6. The method for stabilizing protein C or activated protein C according to claim 1, wherein said adding step comprises first dissolving said protein C or activated protein C in said salt buffer, and then subsequently adding said sodium ion, said at least one amino acid, and said compound thereto.

7. The aqueous buffer solution according to claim 4, wherein 0.0005% to 0.1% w/v of a non-ionic surfactant is present in said aqueous buffer solution.

8. The aqueous buffer solution according to claim 4, wherein 0.0005 to 10% w/v of a non-ionic surfactant in combination with 0.5 to 10% w/v of albumin are present in said aqueous buffer solution.

9. The composition according to claim 5, wherein 0.005 to 1 g of a non-ionic surfactant is present in said composition.

10. The composition according to claim 5, wherein 0.005 to 1 g of a non-ionic surfactant in combination with 5 to 100 g of albumin are present in said composition.

11. A method for stabilizing protein C or activated protein C which comprises adding a salt buffer, sodium ion, at least one amino acid, and a compound selected from the group consisting of a non-ionic surfactant and a mixture of a non-ionic surfactant and albumin to protein C or activated protein C to stabilize protein C or activated protein C.

12. The method according to claim 11, wherein said at least one amino acid is added to a final concentration in a range of 0.005M to 0.1M.

13. The method according to claim 11, wherein said at least one amino acid is a naturally occurring α-amino acid.

14. The method according to claim 13, wherein said at least one amino acid is selected from glycine, alanine, lysine, arginine, aspartic acid, glutamic acid, and mixtures thereof.

15. The method according to claim 11, wherein said non-ionic surfactant is added to a final concentration in a range of 0.0005% w/v to 0.1% w/v.

16. The method according to claim 11, wherein said albumin is added to a final concentration in a range of 0.5% w/v to 10% w/v.

17. The method according to claim 11, wherein said adding step comprises first dissolving said protein C or activated protein C in said buffer, and subsequently adding said sodium ion, said at least one amino acid, and said compound thereto.

18. The method according to claim 1, further comprising the step of lyophilizing the protein C or activated protein C-containing composition.

19. The method according to claim 18, wherein protein C or activated protein C in the lyophilized composition is stable at 15° C. for 30 months or at 60° C. for 11 days.

* * * * *

UNITED STATES PATENT AND TRADEMARK OFFICE
CERTIFICATE OF CORRECTION

PATENT NO. : 5,962,299
DATED : Oct. 5, 1999
INVENTOR(S) : Miyata et al.

It is certified that error appears in the above-identified patent and that said Letters Patent is hereby corrected as shown below:

```
    Cover page, line [86], delete "Apr. 23, 1996"
(both occurrences) and insert therefor --Apr. 29, 1999--
(both occurrences).
```

Signed and Sealed this

Eighteenth Day of July, 2000

*Attest:*

Q. TODD DICKINSON

*Attesting Officer*      Director of Patents and Trademarks